US009918948B2

(12) United States Patent
Lederman et al.

(10) Patent No.: US 9,918,948 B2
(45) Date of Patent: Mar. 20, 2018

(54) METHODS AND COMPOSITIONS FOR TREATING SYMPTOMS ASSOCIATED WITH POST-TRAUMATIC STRESS DISORDER USING CYCLOBENZAPRINE

(75) Inventors: Seth Lederman, New York, NY (US); Herbert Harris, Chapel Hill, NC (US)

(73) Assignee: TONIX PHARMA HOLDINGS LIMITED, Hamilton (BM)

(*) Notice: Subject to any disclaimer, the term of this patent is extended or adjusted under 35 U.S.C. 154(b) by 0 days.

(21) Appl. No.: 12/948,828

(22) Filed: Nov. 18, 2010

(65) Prior Publication Data

US 2011/0124656 A1    May 26, 2011

Related U.S. Application Data

(60) Provisional application No. 61/281,661, filed on Nov. 20, 2009.

(51) Int. Cl.
*A61K 31/01* (2006.01)
*A61K 31/015* (2006.01)
*A61K 31/13* (2006.01)
*A61K 31/131* (2006.01)
*A61K 31/135* (2006.01)

(52) U.S. Cl.
CPC ............ *A61K 31/135* (2013.01); *A61K 31/01* (2013.01); *A61K 31/015* (2013.01); *A61K 31/13* (2013.01); *A61K 31/131* (2013.01)

(58) Field of Classification Search
CPC ...... A61K 31/01; A61K 31/015; A61K 31/13; A61K 31/131
USPC .................................................. 514/252.17
See application file for complete search history.

(56) References Cited

U.S. PATENT DOCUMENTS

| 4,968,507 A | 11/1990 | Zentner et al. |
|---|---|---|
| 5,073,543 A | 12/1991 | Marshall et al. |
| 5,120,548 A | 6/1992 | McClelland et al. |
| 5,439,686 A | 8/1995 | Desai et al. |
| 5,498,421 A | 3/1996 | Grinstaff et al. |
| 5,591,731 A | 1/1997 | Kennedy et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 6,096,331 A | 8/2000 | Desai et al. |
| 6,248,363 B1 | 6/2001 | Patel et al. |
| 6,267,985 B1 | 7/2001 | Chen et al. |
| 6,309,663 B1 | 10/2001 | Patel et al. |
| 6,358,944 B1 | 3/2002 | Lederman |
| 6,383,471 B1 | 5/2002 | Chen et al. |
| 6,395,788 B1 | 5/2002 | Iglehart |
| 6,506,405 B1 | 1/2003 | Desai et al. |
| 6,537,579 B1 | 3/2003 | Desai et al. |
| 6,541,523 B2 | 4/2003 | Iglehart |
| 6,720,001 B2 | 4/2004 | Chen et al. |
| 6,749,868 B1 | 6/2004 | Desai et al. |
| 6,753,006 B1 | 6/2004 | Desai et al. |
| 6,761,903 B2 | 7/2004 | Chen et al. |
| 7,105,486 B2 | 9/2006 | Mickle et al. |
| 7,223,735 B2 | 5/2007 | Mickle et al. |
| 7,532,935 B2 | 5/2009 | Maschino |
| 7,655,630 B2 | 2/2010 | Mickle et al. |
| 7,658,945 B2 | 2/2010 | Singh |
| 7,659,253 B2 | 2/2010 | Mickle et al. |
| 7,659,254 B2 | 2/2010 | Mickle et al. |
| 7,662,787 B2 | 2/2010 | Mickle et al. |
| 7,662,788 B2 | 2/2010 | Mickle et al. |
| 7,671,030 B2 | 3/2010 | Mickle et al. |
| 7,671,031 B2 | 3/2010 | Mickle et al. |
| 7,674,774 B2 | 3/2010 | Mickle et al. |
| 7,678,770 B2 | 3/2010 | Mickle et al. |
| 7,678,771 B2 | 3/2010 | Mickle et al. |
| 7,682,628 B2 | 3/2010 | Singh |
| 7,687,466 B2 | 3/2010 | Mickle et al. |
| 7,687,467 B2 | 3/2010 | Mickle et al. |
| 7,700,561 B2 | 4/2010 | Mickle et al. |
| 7,713,936 B2 | 5/2010 | Mickle et al. |
| 7,718,619 B2 | 5/2010 | Mickle et al. |
| 7,723,305 B2 | 5/2010 | Mickle et al. |
| RE41,884 E | 10/2010 | Garavilla et al. |
| 7,820,788 B2 | 10/2010 | Desai et al. |
| 7,923,536 B2 | 4/2011 | Desai et al. |

(Continued)

FOREIGN PATENT DOCUMENTS

| EP | 2233134 | 9/2010 |
|---|---|---|
| WO | WO-1999018937 | 4/1999 |

(Continued)

OTHER PUBLICATIONS

Aaronson et al., "Defining and measuring fatigue," Image J. Nurs. Sch., 31:45-50 (1999).
Abd el-Fattah et al., "Enhancement of dissolution rate of hydrochlorothiazide via solid dispersion," Pharmazie., 41:790-793 (1986).
Abernethyl et al., "Absolute bioavailability of imipramine: influence of food," Psychopharmacology (Berl.), 83:104-106 (1984).
Amin et al., "Indion 414 as superdisintegrant in formulation of mouth dissolve tablets," Indian Journal of Pharmaceutical Sciences, 68:117-119 (2006).
Amitai et al., "Distribution of amitriptyline and nortriptyline in blood: role of alpha-1-glycoprotein," Ther. Durg Monit., 15:267-273 (1993).

(Continued)

*Primary Examiner* — Yong S. Chong
(74) *Attorney, Agent, or Firm* — Haley Guiliano LLP; James F. Haley, Jr.

(57) ABSTRACT

The present invention relates to methods for the treatment or prevention of symptoms associated with post-traumatic stress disorder, and related pharmaceutical compositions. Of particular interest are pharmaceutical compositions comprising a very low dose of cyclobenzaprine, alone, or in combination with an alpha-1-adrenergic receptor antagonist, a beta-adrenergic antagonist, an anticonvulsant, a selective serotonin reuptake inhibitor or a serotonin-norepinephrine reuptake inhibitor.

11 Claims, No Drawings

(56) References Cited

U.S. PATENT DOCUMENTS

| | | | |
|---|---|---|---|
| 8,093,300 B2 | 1/2012 | Lederman | |
| 8,138,229 B2 | 3/2012 | Desai et al. | |
| 9,474,728 B2 | 10/2016 | Lederman et al. | |
| 9,636,408 B2 | 5/2017 | Nebuloni et al. | |
| 2003/0077227 A1 | 4/2003 | Dugger | |
| 2003/0077297 A1 | 4/2003 | Chen et al. | |
| 2005/0096327 A1 | 5/2005 | Caprathe et al. | |
| 2005/0181041 A1 | 8/2005 | Goldman | |
| 2006/0073189 A1 | 4/2006 | Pinney et al. | |
| 2007/0141144 A1 | 6/2007 | Roberts et al. | |
| 2008/0146672 A1 | 6/2008 | Denton et al. | |
| 2009/0054403 A1* | 2/2009 | Woiwode et al. | 514/214.02 |
| 2009/0098200 A1 | 4/2009 | Krayz et al. | |
| 2009/0275541 A1 | 11/2009 | Sullivan | |
| 2010/0021507 A1 | 1/2010 | Bunick et al. | |
| 2010/0098832 A1 | 4/2010 | Venkatesh et al. | |
| 2010/0247586 A1 | 9/2010 | Hugerth | |
| 2010/0247649 A1 | 9/2010 | Palaparthi et al. | |
| 2010/0266682 A1 | 10/2010 | Davar et al. | |
| 2011/0068511 A1 | 3/2011 | Sowden et al. | |
| 2011/0319389 A1 | 12/2011 | Lederman et al. | |
| 2012/0101154 A1 | 4/2012 | Lederman et al. | |
| 2012/0232159 A1 | 9/2012 | Lederman | |
| 2013/0165511 A1 | 6/2013 | Lederman et al. | |
| 2014/0171515 A1 | 6/2014 | Lederman | |
| 2014/0336264 A1 | 11/2014 | Nebuloni | |
| 2015/0065581 A1 | 3/2015 | Lederman | |
| 2016/0030576 A1 | 2/2016 | Nebuloni | |
| 2017/0239195 A1 | 8/2017 | Nebuloni | |
| 2017/0281568 A1 | 10/2017 | Lederman | |

FOREIGN PATENT DOCUMENTS

| | | |
|---|---|---|
| WO | WO-1999058115 | 11/1999 |
| WO | WO 2001/012174 | 2/2001 |
| WO | WO 2001/012175 | 2/2001 |
| WO | WO-2001089476 | 11/2001 |
| WO | WO-2004035021 | 4/2004 |
| WO | WO 2004/039320 | 5/2004 |
| WO | WO-2005051297 | 6/2005 |
| WO | WO-2007038620 | 4/2007 |
| WO | WO 2009/002770 | 12/2008 |
| WO | WO-2009089494 | 7/2009 |
| WO | WO-2011062614 | 5/2011 |
| WO | WO-2014145156 | 9/2014 |

OTHER PUBLICATIONS

Arnold et al., "Antidepressant treatment of fibromyalgia," Psychosomatics, 41:104-113 (2000).
Bagul, Current Status of Table Disintegrants: A Review, retrieved from [http://www.pharmainfo.net/reviews/current-status-tablet-disintegrantsa-review].
Balant et al., "Prodrugs for the Improvement of Drug Absorption Via Different Routes of Administration," Eur. J. Drug Metab. Pharmacokinet, 15:143-153 (1990).
Balasubramaniam et al., "Effects of superdisintegrants on dissolution of cationic drugs," Dissolution Technologies, 18-25 (2008).
Barker and Blakely, "Identification of a single amino acid, phenylalanine 586, that is responsible for high affinity interactions of tricyclic antidepressants with the human serotonin transporter," Mol. Pharmacol., 50:957-965 (1996).
Barnes et al., "Brainstem noradrenergic system depression by cyclobenzaprine," Neuropharmacology, 19:221-224 (1980).
Bartoli et al., "An atypical case of reverse Takotsubo cardiomyopathy during general anesthesia in a 30-year-old male with post-traumatic stress disorder," J. Cardiothorac Vasc. Anesth., 25:1116-1118 (2011).
Baumann et al., "Amitriptyline pharmacokinetics and clinical response: I. Free and total plasma amitriptyline and nortriptyline," Int. Clin. Psychopharmacol., 1:89-101 (1986).
Bennett et al., "A comparision of cyclobenzaprine and placebo in the management of fibrositis: a double-blind controlled study," Arthritis Rheum., 31:1535-1542 (1988).
Berezhkovskiy, "Prediction of the possibility of the second peak of drug plasma concentration time curve after iv bolus administration from the standpoint of the traditional multi-compartmental linear pharmacokinetics," J. Pharm. Sci., 97:2385-2393 (2008).
Bhatt et al., "Development and validation of amitriptyline and its metabolite in human plasma by ultra performance liquid chromatography—tandem mass spectrometry and its application to a bioequivalence study," Biomedical Chromatography, 24:1247-1254 (2010).
Bhowmik et al., "Fast Dissolving Tablet: An Overview," Journal of Chemical and Pharmaceutical Research, 1:163-177 (2009).
Bi et al., "Mechanism of eutectic formation upon compaction and its effects on tablet properties," Thermochimica Acta, 404:213-226 (2003).
Bickel et al., "Buccal absorption and other properties of pharmacokinetic importance of imipramine and its metabolites," J. Pharm. Pharmacol., 21:160-168 (1969).
Blake et al., "The development of a clinician-administered PTSD scale," Journal of Traumatic Stress, 8:75-90 (1995).
Braithwaite et al., "Plasma concentration of amitriptyline and clinical response," Lancet., 17:1297-1300 (1972).
Breyer-Pfaff et al., "Comparative N-glucuronidation kinetics of ketotifen and amitriptyline by expressed human UDP-glucuronosyltransferases and liver microsomes," Drug Metab. Dispos., 28:869-872 (2000).
Brittain, "A summary of the scholarly activities associated with Center for Pharmaceutical Physics," Journal of Pharmaceutical Physics, vol. 11, Information Healthcare Press, New York (2009).
Brittain, "Profiles of Drug Substances, Excipients, and Related Methodology," Journal of Pharmaceutical Physics, vol. 12, Elsevier Academic Press, Amsterdam (2010).
Bundgaard, "Novel Chemical Approaches in Prodrug Design," Drugs of the Future, 16:443-458 (1991).
Cai et al., "A humanized UGT1 mouse model expressing the UGT1A1*28 allele for assessing drug clearance by UGT1A1-dependent glucuronidation," Drug Metab. Dispos., 38:879-886 (2010).
Campbell Roberts et al., "Quantitative analysis of mannitol polymorphs. X-ray powder diffractometry-exploring preferred orientation effects," J. Pharm. Biomed. Anal., 28:1149-1159 (2002).
Cantini et al., "[Fluoxetin combined with cyclobenzaprine in the treatment of fibromyalgia]," Minerva Med., 85:97-100 (1994) (Abstract only).
Cavaljuga et al., "Therapeutic effects of two antidepressant agents in the treatment of posttraumatic stress disorder (PTSD)," Bosn J. Basic Med. Sci. III, 3:12-16 (2003).
Commissiong et al., "Cyclobenzaprine: a possible mechanism of action for its muscle relaxant effect," Can. J. Physicol. Pharmacol., 59:37-44 (1981).
Cotton and Down, "Cyclobenzaprine hydrochloride," Anal Profiles Drug Subs, 17:41-72 (1988).
Davies et al., "Multiple peaking phenomena in pharmacokinetic disposition," Clinical Pharmacokinetics, 49:351-377 (2010).
Descamps et al., "Transformation of pharmaceutical compounds upon milling and comilling: the role of T(g).," J. Pharm. Sci., 96:1398-1407 (2007).
Dobrinska, "Enterohepatic circulation of drugs," J. Clin. Pharmacol., 29:577-580 (1989).
El-Banna et al., "Physicochemical study of drug binary systems. Part 3: Tolbutamide-urea and tolbutamide-mannitol systems," Pharmazie., 30:788-792 (1975).
El-Banna et al., "The application of solid dispersion technique in the preparation of therapeutic tablets. Part 1: Paracetamol, amylobarbitone, and caffeine tablets," Pharmazie, 32:511-515 (1977).
Ereshefsky et al., "Pharmacokinetic factors affecting antidepressant drug clearance and clinical effect: evaluation of doxepin and imipramine—new data and review," Clin. Chem., 34:863-880 (1988).
FDA Guidance for Industry, Bioavailability and Bioequivalence Studies for Orally Administered Drug Products—General Consid-

(56) References Cited

OTHER PUBLICATIONS eration, US Dept. of Health and Human Services, FDA, Center for Drug Evaluation and Research, pp. 1-23 (2003).
Fossaluzza et al., "Combined therapy with cyclobenzaprine and ibuprofen in primary fibromyalgia syndrome," Int. J. Clin. Pharmacol. Res., 12:99-102 (1992).
Fronczek et al., "Three polymorphs (alpha, beta, and delta) of D-mannitol at 100 K," Acta Crystallographica Section C, 59:o567-o570 (2003).
Fujiwara et al., "Developmental hyperbilirubinemia and CNS toxicity in mice humanized with the UDP glucuronosyltransferase 1 (UGT1) locus," Proc. Natl. Acad. Sci, USA, 107:5024-5029 (2010).
Gai et al., "Bioavailability of a controlled-release cyclobenzaprine tablet and influence of a high fat meal on bioavailability," Int. J. Clin. Pharmacol. Ther., 47:269-274 (2009).
Godfrey, "A guide to the understanding and use of tricyclic antidepressants in the overall management of fibromyalgia and other chronic pain syndromes," Arch. Intern. Med., 156:1047-1052 (1996).
Green et al., "Glucuronidation of amine substrates by purified and expressed UDP-glucuronosyltransferase proteins," Drug Metab. Dispos., 26:860-867 (1998).
Guo et al., "Liquid chromatography-tandem mass spectrometry method for measurement of nicotine N-glucuronide: a marker for human UGT2B10 inhibition," J. Pharm. Biomed. Anal., 55:964-971 (2011).
Hawes, "N+-glucuronidation, a common pathway in human metabolism of drugs with a tertiary amine group," Drug Metab. Dispos., 26:830-837 (1998).
Hiller et al., "Retigabine N-glucuronidation and its potential role in enterohepatic circulation," Drug Metab. Dispos., 27:605-612 (1999).
Honda et al, "Tricyclic analogs cyclobenzaprine, amitriptyline and cyproheptadine inhibit the spinal reflex transmission through 5-HT(2) receptors," Eur. J. Pharmacol., 458:91-99 (2003).
Hucker et al., "Metabolism of cyclobenzaprine in the dog," Drug Metab. Dispos., 6:184-192 (1978).
Hucker et al., "Physiological disposition and metabolism of cyclobenzaprine in the rat, dog, rhesus monkey, and man," Drug Metab. Dispos., 6:659-672 (1978).
Hucker et al., "Plasma levels and bioavailability of cyclobenzaprine in human subjects," J. Clin. Pharmacol., 17:719-727 (1977).
Jorgensen et al., "Pharmacokinetics of amitriptyline infused intravenously in man," Eur. J. Clin. Pharmacol., 10:337-341 (1976).
Kaivosaari et al., "N-glucuronidation of drugs and other xenobiotics by human and animal UDP-glucuronosyltransferases," Xenobiotica., 41:652-669 (2011).
Katz and Dube, "Cyclobenzaprine in the treatment of acute muscle spasm: review of a decade of clinical experience," Clinical Therapeutics, 10:216-228 (1988).
Kobayashi et al., "Cyclobenzaprine, a centrally acting muscle relaxant, acts on descending serotonergic systems," Eur. J. Pharmacol., 311:29-35 (1996).
Kornhuber et al., "Identification of new functional inhibitors of acid sphingomyelinase using a structure-property-activity relation model," J. Med. Chem., 51:219-237 (2008).
Krishnan et al., "The molecular neurobiology of depression," Nature, 455:894-902 (2008).
Kubo et al., "Improvement of dissolution rate and oral bioavailability of a sparingly water-soluble drug, (+/−)-5-[[2-(2-naphthalenylmethyl)-5-benzoxazolyl]-methyl]- 2,4-thiazolidinedione, in co-ground mixture with D-mannitol," Biol. Pharm. Bull., 20:460-463 (1997).
Lee et al., "Transinactivation of the epidermal growth factor receptor tyrosine kinase and focal adhesion kinase phosphorylation by dietary flavonoids: effect on invasive potential of human carcinoma cells," Biochem. Pharmacol., 67:2103-2114 (2004).
Link et al., "Cardiovascular regulation in mice lacking alpha2-adrenergic receptor subtypes b and c," Science, 273:803-805 (1996).
Miles et al., "An investigation of human and rat liver microsomal mycophenolic acid glucuronidation: evidence for a principal role of UGT1A enzymes and species differences in UGT1A specificity," Drug Metab. Dispos., 33:1513-1520 (2005).
Moldofsky et al., "Effects of bedtime very low dose cyclobenzaprine on symptoms and sleep physiology in patients with fibromyalgia syndrome: a double-blind randomized placebo-controlled study," J. Rheum., 38:2653-2663 (2011).
Narang and Sherma, "Sublingual mucosa as a route for systemic drug delivery," Int. J. Pharma., Sci., 3:18-22 (2011).
Ohshima et al., "Tissue distribution and metabolism of amitriptyline after repeated administration in rats," Drug Metab. Dispos., 22:21-25 (1994).
Overo et al., "Kinetics of nortriptyline in man according to a two compartment model," Eur. J. Clin. Pharmacol., 8:343-347 (1975).
Protocol Registration Receipt Jun. 26, 2012, "Comparative Bioavailability of sublingual TNX-102, Oral and Intravenous Cyclobenzaprine in Healthy Adults." ClinicalTrials.gov (2012).
Razaghi et al., "Investigation of cyclobenzaprine hydrochloride release from oral osmotic delivery systems containing a water-swellable polymer," Drug Dev. Ind. Pharma., 28:631-639 (2002).
Rizzi et al.,"Cyclic alternating pattern: a new marker of sleep alteration in patients with fibromyalgia?," J. Rheumatol., 31:1193-1199 (2004).
Rosa et al., "Automatic detection of cyclic alternating pattern (CAP) sequences in sleep: preliminary results," 110:585-592 (1999).
Santandrea et al., "A double-blind crossover study of two cyclobenzaprine regimens in primary fibromyalgia syndrome," J. Int. Med. Res., 21:74-80 (1993).
Shukla et al., "Mouth Dissolving Tablets I: An Overview of Formulation," Technology Scientia Pharmaceutica, 77:309-326 (2009).
Siddegowda et al., "Cyclo-benzaprinium chloride," Acta Crystallogr Sect E Struct Rep Online. Jul. 1, 2011; 67(Pt 7): o1846 (Abstract only).
Singh et al., "Tablet disintegrants: an overview," American Journal of Pharmtech Research, 2:14-23 (2012).
Sutfin et al., "The analysis and disposition of imipramine and its active metabolites in man," Psychoharmacology, 82:310-317 (1984).
Telang et al., "Crystallization of D-mannitol in binary mixtures with NaCl: phase diagram and polymorphism," Pharm. Res., 20:1939-1945 (2003).
Terzano et al., "Atlas, rules, and recording techniques for the scoring of cyclic alternating pattern sleep," Sleep Med., 3:187-199 (2002).
Terzano et al., "Polysomnographic analysis of arousal responses in obstructive sleep apnea syndrome by means of the cyclic alternating pattern," J. Clin. Neurophysiol., 13:145-155 (1996).
Thomas et al., "Sleep as a window into the world of fibromyalgia syndrome," J. Rheumatol., 38:2499-2500 (2011).
Till et al., "Evidence for route dependent biotransformation of cyclobenzaprine hydrochloride," Biopharm. Drug Dispos., 3:19-28 (1982).
Tukey et al., "Human UDP-glucuronosyltransferases: metabolism, expression, and disease," Annu. Rev. Pharmacol. Toxicol., 40:581-616 (2000).
Vaddady et al., "In vitro pharmacokinetic/pharmacodynamic models in anti-infective drug development: focus on TB," Future Med. Chem., 2:1355-1369 (2010).
Wang et al., "Identification of human liver cytochrome P450 isoforms involved in the in vitro metabolism of cyclobenzaprine," Drug Metab. Dispos., 24:786-791 (1996).
Way et al., "Isotope dilution gas chromatographic-mass spectrometric measurement of tricyclic antidepressant drugs. Utility of the 4-carbethoxyhexafluorobutyryl derivatives of secondary amines," J. Anal. Toxicol., 22:374-382 (1998).
Weaver et al., "An instrument to measure functional status outcomes for disorders of excessive sleepiness," Sleep, 20(10):835-43 (1997).
Winchell et al., "Cyclobenzaprine pharmacokinetics, including the effects of age, gender, and hepatic insufficiency," J. Clinical Pharmacol., 42:61-69 (2002).

(56) References Cited

OTHER PUBLICATIONS

Wong et al., "Potential interference of cyclobenzaprine and norcyclobenzaprine with HPLC measurement of amitriptyline and nortriptyline: resolution by GC-MS analysis," J. Anal. Toxicol., 19:218-224 (1995).

Yan et al., "Absolute bioavailability and stereoselective pharmacokinetics of doxepin," Xenobiotica., 32:615-623 (2002).

Zajc et al., "Physical properties and dissolution behaviour of nifedipine/mannitol solid dispersions prepared by hot melt method," Int. J. Pharm., 291:51-58 (2005).

Zelapar Full Prescribing Information, Cardinal Health, Inc., Valeant Pharmaceuticals North America (2006).

Zhang et al., "Concepts and challenges in quantitative pharmacology and model-based drug development," AAPS J., 10:552-559 (2008).

Zhou et al., "Role of human UGT2B10 in N-glucuronidation of tricyclic antidepressants, amitriptyline, imipramine, clomipramine, and trimipramine," Drug Metab. Dispos., 38:863-870 (2010).

Grof et al., "Preliminary Comparative trial of proheptatriene and imipramine in the treatement of depressions. (An intensive and controlled study)," Activitas Nervosa Superior, 7:288-289 (1965).

Vinar et al., "Proheptatriene in depression (extensive study)," Activitas Nervosa Superior, 7:290 (1965).

Caillé et al., "Pharmacokinetics of two lorazepam formulations, oral and sublingual, after multiple doses," Biopharmaceutics and Drug Disposition, 4(1):31-42 (1983).

Cyclobenzaprine (Flexeril), eMedExpert.com—Facts, Oct. 5, 2008 (2 pages), XP055239326,Retrieved from the Internet: URL:http://www.emedexpert.com/facts/cyclobenzaprine-facts.shtml [retrieved on Jan. 7, 2016].

Fibromyalgia: medications for fibromyalgia, Jun. 12, 2008 (3 pages) Tricyclic anti-depressants Citation is not enclosed due to copyright restrictions. A copy may be obtained from the Wayback Machine at https://web.archive.org/web/20080612014615/http://www.spinehealth.com/conditions/fi bromyalgia/fibromyalgia-medications-fibromyalgia.

Price et al., "Single-dose pharmacokinetics of sublingual versus oral administration of micronized 17 beta-estradiol," Obstetrics and Gynecology, 89(3):340-345 (1997).

Rx-s.net Retrieved from the Internet: URL:https://web.archive.org/web/20060516153148/http:l/rx-s.net/weblog/more/cyclobenzaprine_flexerilreg/ [retrieved on Mar. 12, 2013], from 2006 (2 pages).

Ford et al., "Thermal Analysis of Sulphamethoxazole—Sugar Physical Mixes," Drug Development and Industrial Pharmacy, 11(5):1111-1112 (1985).

\* cited by examiner

METHODS AND COMPOSITIONS FOR TREATING SYMPTOMS ASSOCIATED WITH POST-TRAUMATIC STRESS DISORDER USING CYCLOBENZAPRINE

RELATED U.S. PATENT APPLICATION DATA

This patent application claims priority from U.S. provisional patent application No. 61/281,661, filed Nov. 20, 2009.

FIELD OF THE INVENTION

The present invention relates to methods for the treatment or prevention of symptoms associated with post-traumatic stress disorder, and related pharmaceutical compositions. Of particular interest are pharmaceutical compositions comprising a very low dose of cyclobenzaprine, alone, or in combination with an alpha-1-adrenergic receptor antagonist, a beta-adrenergic antagonist, an anticonvulsant, a selective serotonin reuptake inhibitor or a serotonin-norepinephrine reuptake inhibitor.

BACKGROUND OF THE INVENTION

Cyclobenzaprine, or 3-(5H-dibenzo[a,d]cyclohepten-5-ylidene)-N,N-dimethyl-1-propanamine, was first approved by the U.S. Food and Drug Administration in 1977 for the treatment of acute muscle spasms of local origin. (Katz, W., et al., *Cyclobenzaprine in the Treatment of Acute Muscle Spasm: Review of a Decade of Clinical Experience*, Clinical Therapeutics 10:216-228 (1988)). Cyclobenzaprine has also been studied in the treatment of fibromyalgia. In a study of 120 fibromyalgia patients, those receiving cyclobenzaprine (10 to 40 mg) over a 12-week period had significantly improved quality of sleep and pain score. There was also a reduction in the total number of tender points and muscle tightness.

Furthermore, the utility of a very low dose cyclobenzaprine as an agent for improving the quality of sleep, as a sleep deepener, or for treating sleep disturbances has been investigated. The very low dosage regimen was viewed as particularly useful in treating sleep disturbances caused by, exacerbated by or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety or for treating an illness caused by or exacerbated by sleep disturbances, and symptoms of such illness and generalized anxiety disorder. See U.S. Pat. Nos. 6,395,788 and 6,358,944, herein incorporated by reference.

Disturbed sleep is a central feature of post-traumatic stress disorder (PTSD) that is included in two thirds of major symptom clusters in DSM-IV. Several observations suggest that disturbed sleep exacerbates or prolongs PTSD: (1) sleep disturbance in reaction to trauma is a marker for the development of PTSD; (2) the severity of established PTSD correlates with the severity of sleep disturbance; (3) sleep arousals and nightmares are core symptoms; and (4) at least one pharmacologic agent (prazosin) that targets the sleep disturbance in PTSD administered at bedtime not only improves sleep but also improves global clinical status. Thus, it is important to develop new methods and pharmaceutical compositions that will attenuate arousal signals that disrupt sleep, reduce PTSD nightmares and other measures of disturbed sleep, and improve PTSD global symptoms with minimal side effects.

SUMMARY OF THE INVENTION

In one aspect the invention is a method for treating a sleep disturbance or a non-sleep disturbance associated with post-traumatic stress disorder (PTSD). The method comprises administering to a human in need of such treatment a pharmaceutical composition comprising cyclobenzaprine in a therapeutically effective amount and a therapeutically effective carrier, wherein such treatment ameliorates or eliminates the symptoms. The cyclobenzaprine may be administered at a dose between 0.1 mg to 50 mg/day and preferably at a very low dose of less than 5 mg/day. The method may further entail administering sequentially or concurrently a drug selected from the group consisting of an alpha-1-adrenergic receptor antagonist, a beta-adrenergic antagonist, an anticonvulsant, a selective serotonin reuptake inhibitor or a serotonin-norepinephrine reuptake inhibitor. Exemplary drugs include prazosin, sertraline, paroxetine, fluoxetine, citalopram and escitalopram. The pharmaceutical compositions may be administered in combination with psychotherapeutic intervention.

In other aspects, the invention is a method for preventing the development (either initiation, consolidation or perpetuation) of a post-traumatic stress disorder (PTSD) symptom following a traumatic event. The method comprises administering to a human in need of such treatment within certain time intervals of the traumatic event a pharmaceutical composition comprising cyclobenzaprine in a therapeutically effective amount and a therapeutically effective carrier, wherein such treatment eliminates or ameliorates the PTSD symptom. The cyclobenzaprine may be administered at between 0.1 mg to 50 mg/day, and preferably at a very low dose of less than 5 mg/day. The method may further entail administering sequentially or concurrently a drug selected from the group consisting of an alpha-1-adrenergic receptor antagonist, a beta-adrenergic antagonist, an anticonvulsant, a selective serotonin reuptake inhibitor or a serotonin-norepinephrine reuptake inhibitor. The pharmaceutical compositions may be administered in combination with psychotherapeutic intervention.

In a further aspect, the invention is a pharmaceutical composition comprising a therapeutically effective amount of cyclobenzaprine in combination with a drug selected from the group consisting of an alpha-1-adrenergic receptor antagonist, a beta-adrenergic antagonist, and an anticonvulsant. The amount of cyclobenzaprine in the pharmaceutical composition is preferably less than 5 mg.

In yet another aspect, the invention is a method for selecting an effective dose of cyclobenzaprine to be administered to a human in need of such treatment. The method comprises obtaining a genetic sample from said human and identifying the CYP3A, CYP1A2, CYP3A4 or CYP2G6 genotype of said human, for example by using a gene chip or a PCR technique to identify the alleles of one or more of the genes. Different alleles metabolize cyclobenzaprine at different speeds. For individuals having a cytochrome allele identified to metabolize cyclobenzaprine quickly a higher dose of cyclobezaprine is administered. For individuals having an isoform identified to metabolize cyclobenzaprine slowly a lower dose of cyclobenzaprine is administered.

DETAILED DESCRIPTION OF THE INVENTION

In one aspect the invention is a method for treating or preventing post-traumatic stress disorder (PTSD) or one of its symptoms. The method comprises administering to a human in need of such treatment a pharmaceutical composition comprising cyclobenzaprine in a therapeutically effective amount and a therapeutically effective carrier. The symptom may be a sleep disturbance or a non-sleep disturbance.

The term a "sleep disturbance" covers symptoms including difficulty falling asleep, early morning awakening, nightmares, and sleep of poor quality. The quality of sleep ("sleep disturbance") may be determined, inter alia, by asking the patient if he/she awakened tired or nonrefreshed "never," "seldom," "often or usually," or "always." Replies of "often or usually" or "always" may be scored as positive and other replies as negative. Patients' reports of well-being or relief from "zombie" or "spacey" feelings, feelings of being "run down," and having difficulty concentrating during waking hours are indications of better quality of sleep or deep, refreshing sleep. A rating scale commonly used to assess sleep quality is the Functional Outcomes of Sleep Questionnaire (FOSQ) is described in Weaver et al., (1997), *An instrument to measure functional status outcomes for disorders of excessive sleepiness.* 20(10):835-43.

The term a "non-sleep disturbance" covers symptoms including recurrent and intrusive distressing recollections of the event, including images, thoughts, or perceptions; acting or feeling as if the traumatic event were recurring (includes a sense of reliving the experience, illusions, hallucinations, and dissociative flashback episodes, including those that occur upon awakening or when intoxicated; intense psychological distress at exposure to internal or external cues that symbolize or resemble an aspect of the traumatic event; physiological reactivity on exposure to internal or external cues that symbolize or resemble an aspect of the traumatic event; persistent avoidance of stimuli associated with the trauma and numbing of general responsiveness (not present before the trauma), as indicated by three (or more) of the following: (1) difficulty falling or staying asleep, (2) irritability or outbursts of anger, (3) difficulty concentrating, (4) hypervigilance, or (5) an exaggerated startle response; persistent symptoms of increased arousal (not present before the trauma), as indicated by two (or more) of the following: difficulty falling or staying asleep, irritability or outbursts of anger, difficulty concentrating, hypervigilance, exaggerated startle response. These symptoms are commonly measured using the Clinician Administered PTSD Scale (Blake et al., (1995). *The development of a clinician-administered PTSD scale.* Journal of Traumatic Stress, 8, 75-90).

"Cyclobenzaprine" includes cyclobenzaprine or a metabolite thereof, prodrugs of cyclobenzaprine or a metabolite thereof. Metabolites of cyclobenzaprine useful according to the methods of this invention are metabolites that have substantially the same activity or better as cyclobenzaprine in alleviating PTSD symptoms. Cyclobenzaprine metabolites that may be useful according to this invention include CBP 10,11-trans-dihydriol, N-desmethyl-2-hydroxycyclobenzaprine, 3-hydroxycyclobenzaprine, N-desmethylcyclobezaprine cyclobenzaprine N-oxide or a chiral isomer of these metabolites. A prodrug of cyclobenzaprine is a derivative of cyclobenzaprine that is metabolized in vivo into the active agent. Prodrugs useful according to this invention are those that have substantially the same activity or better than cyclobenzaprine in treating or preventing the symptoms of PTSD. Methods for making prodrugs are readily known in the art (e.g., Balant, L. P., *Prodrugs for the Improvement of Drug Absorption Via Different Routes of Administration,* Eur. J. Drug Metab. Pharmacokinet. 15:143-153 (1990); and Bundgaard, H., *Novel Chemical Approaches in Prodrug Design, Drugs of the Future* 16:443-458 (1991); incorporated by reference herein).

As used herein, a "therapeutically effective amount" of cyclobenzaprine for the purposes of this invention refers to the amount of the compound that prevents or alleviates or eliminates or interferes with one of the symptoms associated with PTSD. A physician can readily determine when symptoms are prevented or alleviated or eliminated, for example through clinical observation of a subject, or through reporting of symptoms by the subject during the course of treatment. One skilled in the art can readily determine an effective amount of a cyclobenzaprine to be administered, by taking into account factors such as the size, weight, age and sex of the subject, the extent of disease penetration or persistence and severity of symptoms, and the route of administration. Generally, a therapeutically effective amount of cyclobenzaprine administered to a subject is between 0.1 mg to about 50 mg/day, between 0.5 to about 30 mg/day, or between 1 mg and 20 mg/day. Higher or lower doses are also contemplated.

In one embodiment the cyclobenzaprine is administered at a very low dose to minimize side effects observed at higher doses. The very low doses include doses of less than 5 mg/day or less than 2.5 mg/day. Even lower doses are also contemplated. Generally, cyclobenzaprine therapy can be carried out indefinitely to alleviate the symptoms of interest and frequency of dosage may be changed to be taken as needed. The period of treatment should be carried out for as long as necessary to alleviate one or more of the PTSD symptoms and the cyclobenzaprine administered at nighttime and at an appropriate dose.

In another embodiment of the invention, cyclobenzaprine is administered in combination with a drug which may further alleviate the symptoms of PTSD. The drugs may be administered sequentially or concurrently with the cyclobenzaprine. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary selective serotonin reuptake inhibitors or serotonin-norepinephrine reuptake inhibitors include, but are not limited to, buproprion (at a dose between about 105 mg and 450 mg/day), citalopram (at a dose between about 10 mg and 40 mg/day), desvenlafaxine (at a dose between about 50 mg and 400 mg/day), duloxetine (at a dose between about 40 mg and 120 mg/day), escitalopram (at a dose between about 10 mg and 20 mg/day), fluoxetine (at a dose between about 20 mg and 80 mg/day), fluvoxamine (at a dose between about 100 mg and 300 mg/day), milnacipran (at a dose between about 30 mg and 200 mg/day), paroxetine (at a dose between about 20 mg and 50 mg/day), sertraline (at a dose between about 50 mg and 200 mg/day), tradodone (at a dose between about 150 mg and 600 mg/day), and venlafaxine (at a dose between about 75 mg and 225 mg/day), Exemplary anticonvulsants include, but are not limited to carbamazepine (at a dose between about 400 mg and 1200 mg/day), gabapentin (at a dose between about 900-1800 mg/day), lamotrigine (at a dose between about 100 mg and 400 mg/day), oxcarbazepine (at a dose between about 1200 mg and 2400 mg/day), pregabalin (at a dose between about 150 mg and 600 mg/day), tiagabine (at a dose between about 32 mg and 56 mg/day), topiramate (at a dose between about 200 mg and 400 mg/day), and valproate (at a dose between about 1200 mg and 1500 mg). Exemplary alpha-1-adrenergic receptor antagonists include, but are not limited to, prazosin administered at a dose of between about 0.5 mg to 15 mg/day.

In another aspect, the invention may be employed for treating or preventing the development (either the initiation, consolidation or perpetuation) of a PTSD symptom following a traumatic event. A traumatic event is defined as a direct personal experience that involves actual or threatened death or serious injury, or other threat to one's physical integrity; or witnessing an event that involves death, injury, or a threat to the physical integrity of another person; or learning about unexpected or violent death, serious harm, or threat of death or injury experienced by a family member or other close associate. Traumatic events that are experienced directly include, but are not limited to, military combat, violent personal assault (sexual assault, physical attack, robbery, mugging), being kidnapped, being taken hostage, terrorist attack, torture, incarceration as a prisoner of war or in a concentration camp, natural or manmade disasters, severe automobile accidents, or being diagnosed with a life-threatening illness. For children, sexually traumatic events may include developmentally inappropriate sexual experiences without threatened or actual violence or injury. Witnessed events include, but are not limited to, observing the serious injury or unnatural death of another person due to violent assault, accident, war, or disaster or unexpectedly witnessing a dead body or body parts. Events experienced by others that are learned about include, but are not limited to, violent personal assault, serious accident, or serious injury experienced by a family member or a close friend; learning about the sudden, unexpected death of a family member or a close friend; or learning that one's child has a life-threatening disease. The disorder may be especially severe or long lasting when the stressor is of human design (e.g., torture, rape).

The initiation of a PTSD symptom occurs immediately following the traumatic event during which the symptoms of PTSD appear and become increasingly severe. It is thought that there is a kind of "learning" or reinforcement process in which the memories of the trauma are engrained in the mind. As these memories become more fixed, symptoms such as flashbacks and nightmares grow in severity and frequency. It is though that interventions during this critical time may prevent some patients from developing fully blown PTSD. The consolidation of a PTSD symptom typically occurs during the weeks and months following a traumatic event. A person's memories of that event become consolidated into highly vivid and concrete memories that are re-experienced with increasing frequency either as flashbacks or nightmares. During this time hyperarousal symptoms and avoident behavior become increasingly severe and disabling. The perpetuation of a PTSD symptom occurs once traumatic memories are consolidated, and the reexperiencing symptoms (flashbacks and nightmares) and the hyperarousal symptoms become persistent and remain at a level that is functionally disabling to the patient.

By the method of the invention, the different phases of PTSD development may be treated with a pharmaceutical composition comprising cyclobenzaprine at different time intervals after the traumatic event. For example to treat the initiation phase of PTSD cyclobenzaprine needs to be administered to a subject in need soon after the traumatic event, for example within the first week, within the second week, within the third week or within the forth week or longer. Whereas to treat the consolidation phase of PTSD cyclobenzaprine has to be administered later after the traumatic event and later during the development of the symptoms, for example within the first month, within the second month or within the third month or longer. Typically to treat the perpetuation phase of PTSD the cyclobenzaprine is administered 3 months or longer after the traumatic event, for example within the third month, within the fourth month, within the fifth month or longer. As a result of cyclobenzaprine treatment at the initiation, consolidation, or perpetuation phase, PTSD symptoms will be ameliorated or be eliminated.

The method comprises administering to a human in need of such treatment a pharmaceutical composition comprising cyclobenzaprine in a therapeutically effective amount and a therapeutically acceptable carrier. The therapeutically effective amount of cyclobenzaprine administered to a subject is between 0.1 mg to about 50 mg/day, between 0.5 to about 30 mg/day, or between 1 mg and 20 mg/day. Higher or lower doses are also contemplated. In one particular embodiment the cyclobenzaprine is administered at a very low dose to minimize side effects observed at higher doses. The very low doses include doses of less than 10 mg/day or less than 5 mg/day or less than 2.5 mg/day. Even lower doses are also contemplated. In another embodiment of the invention, cyclobenzaprine is administered in combination with a drug which may further alleviate the symptoms of PTSD. The drugs may be administered sequentially or concurrently with the cyclobenzaprine. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary selective serotonin reuptake inhibitors or serotonin-norepinephrine reuptake inhibitors include, but are not limited to, buproprion (at a dose between about 105 mg and 450 mg/day), citalopram (at a dose between about 10 mg and 40 mg/day), desvenlafaxine (at a dose between about 50 mg and 400 mg/day), duloxetine (at a dose between about 40 mg and 120 mg/day), escitalopram (at a dose between about 10 mg and 20 mg/day), fluoxetine (at a dose between about 20 mg and 80 mg/day), fluvoxamine (at a dose between about 100 mg and 300 mg/day), milnacipran (at a dose between about 30 mg and 200 mg/day), paroxetine (at a dose between about 20 mg and 50 mg/day), sertraline (at a dose between about 50 mg and 200 mg/day), tradodone (at a dose between about 150 mg and 600 mg/day), and venlafaxine (at a dose between about 75 mg and 225 mg/day), Exemplary anticonvulsants include, but are not limited to carbamazepine (at a dose between about 400 mg and 1200 mg/day), gabapentin (at a dose between about 900-1800 mg/day), lamotrigine (at a dose between about 100 mg and 400 mg/day), oxcarbazepine (at a dose between about 1200 mg and 2400 mg/day), pregabalin (at a dose between about 150 mg and 600 mg/day), tiagabine (at a dose between about 32 mg and 56 mg/day), topiramate (at a dose between about 200 mg and 400 mg/day), and valproate (at a dose between about 1200 mg and 1500 mg). Exemplary alpha-1-adrenergic receptor antagonists include, but are not limited to, prazosin administered at a dose of between about 0.5 mg to 15 mg/day.

In a further aspect, the invention is a pharmaceutical composition. The pharmaceutical composition comprises a therapeutically effective amount of cyclobenzaprine in combination with a drug selected from the group consisting of an alpha-1-adrenergic receptor antagonist, a beta-adrenergic antagonist, and an anticonvulsant.

Generally, the amount of cyclobenzaprine in the pharmaceutical composition is between 0.1 mg to about 50 mg, between 0.5 to about 30 mg, or between 1 mg and 20 mg. Higher or lower doses are also contemplated. In one particular embodiment the amount of cyclobenzaprine is very low to minimize side effects observed with higher amounts. The very low amounts are of less than 10 mg or less than 5 mg or less than 2.5 mg. Even lower amounts are also contemplated. In another embodiment of the invention, cyclobenzaprine is combined with a drug which may further alleviate the symptoms of PTSD. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary anticonvulsants include, but are not limited to carbamazepine (400 mg to 1200 mg), gabapentin (900 mg to 1800 mg), lamotrigine (100 mg to 400 mg), oxcarbazepine (1200 mg to 2400 mg), pregabalin (150 mg to 600 mg), tiagabine (32 mg to 56 mg), topiramate (200 mg to 400 mg), and valproate (1200 mg to 1500 mg). An exemplary alpha-1-adrenergic receptor antagonists includes, but is not limited to, prazosin in the amount of 0.5 mg to 15 mg. An exemplary selective serotonin reuptake inhibitor is escitalopram (in the amount of 10 mg and 20 mg).

Any suitable route of administration may be employed for providing the patient with an effective dosage of cyclobenzaprine. For example, buccal, oral, rectal, parenteral, transdermal, subcutaneous, sublingual, intranasal, intramuscular, intrathecal and the like may be employed as appropriate. The term parenteral as used herein includes subcutaneous, intracutaneous, intravenous, intramuscular, intra-articular, intrasynovial, intrasternal, intrathecal, intralesional and intracranial injection or infusion techniques. Dosage forms include tablets, such as scored tablets, coated tablets, or orally dissolving tablets; thin films, caplets, capsules (e.g. hard gelatin capsules), troches, dragees, dispersions, suspensions, solutions, patches and the like, including sustained release formulations well known in the art. In one preferred embodiment, the dosage form is an orally dissolving tablet or a thin film.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices. Pharmaceutical compositions of the invention for parenteral administration can take the form of an aqueous or nonaqueous solution, dispersion, suspension or emulsion. In preparing pharmaceutical compositions of the invention for parenteral administration, cyclobenzaprine can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of cyclobenzaprine. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the invention for oral administration, cyclobenzaprine can be combined with one or more solid or liquid inactive ingredients to form tablets, capsules, pills, powders, granules or other suitable oral dosage forms. For example, cyclobenzaprine can be combined with at least one pharmaceutically acceptable carrier such as a solvent, filler, binder, humectant, disintegrating agent, solution retarder, absorption accelerator, wetting agent absorbent or lubricating agent. In one embodiment, cyclobenzaprine is combined with carboxymethylcellulose calcium, magnesium stearate, mannitol or starch, and is formed into tablets by conventional tableting methods.

Pharmaceutical compositions of the invention can be formulated so as to provide buccal absorption including thin film formulations and orally dissolving tablets to provide faster absorption than the oral/GI route and to bypass first-pass hepatic metabolism of cyclobenzaprine by cytochrome P-450 3A4 as a CYP3A substrate. Preferably, a controlled-release pharmaceutical composition of the invention is capable of releasing cyclobenzaprine into a subject at a rapid onset, so as to maintain a substantially constant or desired pharmacological activity for a given period of time, reduce or remove the effect of food on absorption, and to provide elimination of the drug and metabolites from the body with a reduced terminal elimination phase.

Pharmaceutical compositions of the invention can also be formulated so as to provide controlled-release of cyclobenzaprine upon administration of the composition to a subject. Preferably, a controlled-release pharmaceutical composition of the invention is capable of releasing cyclobenzaprine into a subject at a desired rate, so as to maintain a substantially constant or desired pharmacological activity for a given period of time. As used herein, a "controlled-release component" is a compound such as a lipid or mixture of lipids, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise cyclobenzaprine and a controlled-release component. As used herein, a "controlled-release component" is a compound such as a polymer, polymer matrix, gel, permeable membrane, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, cyclobenzaprine is incorporated into a sol-gel matrix that is a solid at room temperature. This sol-gel matrix is implanted into a subject having a body temperature high enough to induce gel formation of the sol-gel matrix, thereby releasing the active ingredient into the subject.

In one embodiment, pharmaceutical compositions of the invention may comprise cyclobenzaprine and components that form micelles. Micelles containing cyclobenzaprine in the stomach and proximal small intestine facilitate absorption. Example of a micelle-component which is activated by exposure to a certain temperature is found in U.S. Pat. Nos. 6,761,903; 6,720,001; 6,383,471; 6,309,663; 6,267,985; and 6,248,363, incorporated herein by reference. In this embodiment, cyclobenzaprine is incorporated into a soft-gel capsule. Such components may mimic the augmentation of absorption termed the "food effect", and such formulations may provide more predictable absorption by eliminating the "food effect" from dietary sources.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The magnitude of a prophylactic or therapeutic dose of the active ingredient (i.e., cyclobenzaprine or metabolite thereof) in the prevention or treatment of a human will vary with the type of affliction, the severity of the patient's affliction and the route of administration. The dose and dose frequency will also vary according to the age, weight and response of the individual patient. However, the dosage will not equal or exceed 5 mgs per day. In a preferred embodiment, one dose is given at bed time or up to several hours before bedtime to facilitate the achievement of deep, refreshing sleep. Bedtime may be any hour of the day at which a person engages in the most extensive period of sleep.

Any of the methods of treatment described above may be combined with psychotherapeutic intervention to improve the outcome of the treatment. Of particular interest is psychotherapeutic intervention directed at either modifying traumatic memories reducing emotional responses to traumatic memories, and including: psychological debriefing, cognitive behavior therapy and eye movement desensitization and reprocessing, systematic desensitization, relaxation training, biofeedback, cognitive processing therapy, stress inoculation training, assertiveness training, exposure therapy, combined stress inoculation training and exposure therapy, combined exposure therapy and relaxation training and cognitive therapy. In each case, the goal of the intervention involves either modifying traumatic memories or reducing emotional responses to traumatic memories. The intended result is generally improvement as evidenced in terms of reducing intrusive combat memories, physiological responding, anxiety, depression and feelings of alienation.

A pharmacogenomic test to measure cytochrome CYP3A4, CYP1A2, CYP3A and CYP2G6 may be used to predict the metabolism of cyclobenzaprine by certain patients in personalized medicine. Thus, the invention is a method for selecting an effective dose of cyclobenzaprine to be administered to a human in need of such treatment to correct for variations in cyclobenzaprine metabolism. The method comprises obtaining a genetic sample from said human and identifying the CYP1A2, CYP3A4, CYP3A or CYP2G6 genotype of said human, for example by using a gene chip or a PCR technique, to identify the alleles of one or more of the genes. Different alleles metabolize cyclobenzaprine at different speeds. For individuals having a cytochrome allele identified to metabolize cyclobenzaprine quickly a higher dose of cyclobezaprine is administered. For individuals having an allele identified to metabolize cyclobenzaprine slowly a lower dose of cyclobenzaprine is administered. The genetic test can be sold as a kit with the product to physicians/lab testing services.

In order that this invention to be more fully understood, the following examples are set forth. These examples are for the purpose of illustration only and are not to be construed as limiting the scope of the invention in any way. The practice of the invention is illustrated by the following non-limiting examples.

EXAMPLES

Example 1

Tablet Formulation

A typical oral formulation for coated tablets consists of the following:

Formula quantity per tablet (mg.) cyclobenzaprine 1.0, lactose 74.0, corn starch 35.0, water (per thousand tablets) 30.0 ml, magnesium stearate 1.0, corn starch 25.0

The active ingredient (cyclobenzaprine) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration.

Tablets are coated by standard aqueous or nonaqueous techniques. For example, 2.5 mg of hydroxypropymethylcellulose can be dissolved in 25 mg of deionized water. An aqueous (10 mg) suspension of 1.88 mg talc, 0.5 mg of titanium dioxide, 0.1 mg of yellow iron oxide, and 0.02 mg of red iron oxide is stirred into this solution. The coating suspension is sprayed on the tablets and the coated tablets are dried overnight at 45.degree. C.

Example 2

Development of an Optimized Gelcap Formulation of VLD Cyclo for PTSD Sleep Disturbance We are developing a novel gelcap (KRL103) that employs a specific mixture of lipids to form micelles containing cyclobenzaprine that is expected to speed upper GI absorption, increase efficiency of absorption (in stomach and proximal small intestine); decrease or eliminate food effect (which is 20% for the Amrix formulation of cyclobenzaprine) and speed elimination (since lower GI absorption may prolong the terminal elimination phase in existing formulations). The gelcap formulation is expected to result in increased dosage precision; decreased potential for morning "hangover"; and potentially more rapid induction of sleep.

Example 3

Randomized Double Blind Placebo-controlled Fixed Dose Study of Gelcap Formulation in PTSD We will evaluate the effects of KRL103 on sleep architecture, subjective measures of sleep quality, nightmares and general symptoms of PTSD on VA patients with persistent PTSD. KRL103 will be compared to placebo during a 4 week evaluation period, which will include three nights of polysomnography (PSG) and weekly assessments of self- and clinician-administered ratings. Eligible subjects meeting DSM-IV criteria for PTSD will undergo a baseline assessment at the end of medication washout. Following screening and baseline evaluation, eligible patients will be randomized 1:1 to receive either KRL103 3.5 mg, or placebo once daily at bedtime for 4 weeks. The sleep related PTSD symptoms will be quantified with the Cyclic Alternating Pattern in Sleep (CAPS) "recurrent distressing dreams" and "disturbed sleep" items, a non-nightmare distressed awakenings scale, the PTSD Dream Rating Scale (PDRS), the PTSD Checklist-Civilian (PCL-C), and the Clinical Global Impression of Improvement (CGI-I). The effect of KRL103 on sleep will be assessed both subjectively (CAPS) and objectively through the use of overnight PSG. The PSG will be performed at prestudy screening, at baseline, and at Weeks 2 and 4 (on treatment). Sleep records will be scored under blinded conditions in 30-second epochs according to standard criteria by a central reader. Additional studies will involve active-duty military personnel with consolidation-phase PTSD and civilians with PTSD from automobile accident associated trauma.

Example 4

Treatment of Sleep and Non-sleep Disturbances During the Initiation of PTSD

A patient is brought to medical attention within one week of experiencing a significantly traumatic event. The patient is immediately started on cyclobenzaprine administered orally at a dose of 1 to 4 mg given at bedtime either alone, or in combination with sertraline, or an alpha blockers such as prazosin. Over the next three months the patient experiences occasional nightmares and possibly flashbacks to the traumatic experience However, these are not associated with the same degree of psychological distress and physiological arousal as would be the case in untreated patients. Sleep may, to some extent, be disrupted by nightmares, but on the whole sleep is substantially better in quality than would be the case in untreated patients. In addition, daytime fatigue is diminished as compared to untreated patients. During a three-month time interval, the frequency of nightmares or flashbacks declines eventually approaching zero. No avoiding behavior or hyperarousal symptoms develop. The patient is able to function at, or near, baseline throughout this process. This contrasts sharply with untreated patients who typically experience frequent nightmares and flashbacks that are associated with very strong emotional distress. Within a few months of the traumatic event, patterns of avoidant behavior and hyperarousal/hypervigilance develop which contribute to significant functional impairment. Treatment with cyclobenzaprine during the initiation phase of the disease greatly attenuates these symptoms and enables the patient eventually to return to baseline.

Example 5

Treatment of Sleep and Non-sleep Disturbances During Consolidation of PTSD

A patient comes to medical attention within one to three months following a significantly traumatizing event. At this point the usual natural history of the disease has progressed to the point where patients typically experience recurrent nightmares associated with their traumatic events. These result in highly fragmented sleep, insomnia, early-morning awakening, and associated daytime fatigue and cognitive impairment. In addition patients at this stage in the evolution of their disorder have a constellation of daytime symptoms consisting of hyperarousal, hypervigilance, exaggerated startle, and other signs of overactive vigilance behaviors. Also, at this point patients begin to engage in avoidant behaviors such that they actively avoided people and circumstances that might trigger memories of the traumatic event. Lastly, patients begin to experience daytime reexperiencing of their traumatic events in the form of flashbacks. Patients started on cyclobenzaprine at doses of 1 to 4 mg administered orally at bedtime either alone, or in combination with sertraline, or prazosin will experience significant improvements in all sleep associated symptomatology including reduce nightmares, decreases in distress associated with nightmares, less insomnia, and improvements in daytime fatigue and cognitive function. In addition, daytime symptoms not associated with sleep will be greatly reduced or eliminated. These include hyperarousal, hypervigilance, exaggerated startle, and avoidant behavior. Changes in each of these symptom domains will produce improvement in social and occupational functioning.

Example 6

Treatment of Sleep and Non-sleep Disturbances During Perpetuation of PTSD

In patients with well-established PTSD that has been present for greater than three months. At this point the usual natural history of the disease has progressed to the point where patients typically experience recurrent nightmares and daytime flashbacks associated with highly vivid memories of the traumatic event. These result in highly fragmented sleep, insomnia, early-morning awakening, and associated daytime fatigue and cognitive impairment. In addition patients at this stage in the evolution of their disorder have a constellation of daytime symptoms consisting of hyperarousal, hypervigilance, exaggerated startle, and other signs of overactive vigilance behaviors. Also, at this point patients begin to engage in avoidant behaviors such that they actively avoided people and circumstances that might trigger memories of the traumatic event. Lastly, patients begin to experience daytime reexperiencing of their traumatic events in the form of flashbacks. Patients started on cyclobenzaprine at doses of 1 to 4 mg administered orally at bedtime either alone, or in combination with a sertraline, or prazosin, will experience significant improvements in all sleep associated symptomatology including reduce nightmares, decreases in distress associated with nightmares, less insomnia, and improvements in daytime fatigue and cognitive function. In addition, daytime symptoms not associated with sleep will be greatly reduced or eliminated. These include hyperarousal, hypervigilance, exaggerated startle, and avoidant behavior. Changes in each of these symptom domains will produce improvement in social and occupational functioning.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

We claim:

1. A method for treating post-traumatic stress disorder (PTSD) following a traumatic event, comprising: administering to a human in need of such treatment a pharmaceutical composition comprising cyclobenzaprine in a therapeutically effective amount and a therapeutically effective carrier, wherein such treatment eliminates or ameliorates the PTSD.

2. The method of claim 1, wherein the amount of cyclobenzaprine administered is between 0.1 mg and 50 mg/day.

3. The method of claim 2, wherein the amount of cyclobenzaprine administered is between 0.5 mg and 30 mg/day.

4. The method of claim 3, where the amount of cyclobenzaprine administered is between 1 mg and 20 mg/day.

5. The method of claim 1, wherein the amount of cyclobenzaprine administered is less than 5 mg/day.

6. The method of claim 5, wherein the amount of cyclobenzaprine administered is less than 2.5 mg/day.

7. The method of claim 1, wherein the method further comprises administering sequentially or concurrently a drug selected from the group consisting of an alpha-1-adrenergic receptor antagonist, a beta-adrenergic antagonist, an anticonvulsant, a selective serotonin reuptake inhibitor and a serotonin-norepinephrine reuptake inhibitor.

8. The method of claim 7, wherein the alpha-1-adrenergic receptor antagonist is prazosin.

9. The method of claim 8, wherein the selective serotonin reuptake inhibitor is sertraline, paroxetine, fluoxetine, citalopram or escitalopram.

10. The method of claim 1, wherein the pharmaceutical composition is administered as an orally dissolving tablet or as a thin film formulation.

11. The method of claim 1, wherein the pharmaceutical composition is administered in combination with psychotherapeutic intervention.

* * * * *